United States Patent
Aruin

(12) 
(10) Patent No.: US 6,234,982 B1
(45) Date of Patent: *May 22, 2001

(54) APPARATUS AND METHOD FOR ASSESSMENT AND FEEDBACK TRAINING OF STEP WIDTH COORDINATION

(76) Inventor: Alexander S. Aruin, Two Wheaton Center #312, Wheaton, IL (US) 60187

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/054,266

(22) Filed: Apr. 3, 1998

(51) Int. Cl.$^7$ ................................................. A61B 5/103
(52) U.S. Cl. ............................................................ 600/595
(58) Field of Search .................................... 600/587, 595, 600/594, 437

(56) References Cited

U.S. PATENT DOCUMENTS

| | | | |
|---|---|---|---|
| 3,208,062 | * 9/1965 | Gregory | 340/689 |
| 4,191,949 | 3/1980 | Myers . | |
| 4,557,275 | 12/1985 | Demsey, Jr. et al. . | |
| 4,938,476 | 7/1990 | Brunelle . | |
| 5,337,758 | * 8/1994 | Moore et al. | 600/594 |
| 5,433,201 | 7/1995 | Manthey . | |

* cited by examiner

Primary Examiner—Cary O'Connor
Assistant Examiner—Pamela Wing
(74) Attorney, Agent, or Firm—Marshall, O'Toole, Gerstein, Murray & Borun

(57) ABSTRACT

The apparatus provides feedback training of the proper base support during gait therapy of patients with neurological disorders. The apparatus produces recognizable by the user signals in response to change in distance between legs of the user or between the body of the user and an assisstive device. The apparatus is adjustable to desire distance between two legs or a distance between an assisstive device and the user's body, and to a particular exercise protocol.

33 Claims, 5 Drawing Sheets

APPARATUS AND METHOD FOR ASSESSMENT AND FEEDBACK TRAINING OF STEP WIDTH COORDINATION

FIELD OF THE INVENTION

This invention relates to equipment for physical therapy. More specifically it relates to a portable device that is placed on the user's body and which provides the user with information concerning a distance between two feet, therefore resulting in more efficient treatment of gait disorders related to decreased base of support.

SUMMARY OF THE INVENTION

The stability of the human body depends on several factors including size of base support, mass of the body and location of its center of gravity and the location of the projection of the line of gravity within the base, etc.

To be stable while walking or standing, the force line from the center of mass of the body has to fall within the base of support. The base of support is the area bounded by a line connecting the perimeter of all points touching the ground. For a freestanding person with no ambulation aid the entire area between two feet represents the base of support. The human body is at its most unstable during one leg stance or while the feet are close together and parallel. Enlarging the base of support by moving feet apart or using a cane, crutches or walker, can increase stability.

The base of support changes with age: healthy old people usually demonstrate a larger base of support than young adults do. Clinicians often refer balance problems in patients with decreased base of support related to impossibility of maintaining of proper distance between feet. Neurological impairments and weakness of leg muscles, in particular, leg abductors are described as a main source of difficulties of controlling this parameter by patients themselves.

Special treatment directed towards increase muscle strength, range of motion, and endurance may provide functional improvement. However, for a significant number of patients with brain damage, decreased level of attention, motivation, etc. it is difficult to difficult to achieve therapeutic goals without special efforts of both, the patient and a physical therapist. Such patients do not demonstrate significant improvement of gait performance even if the physical therapist contributes enormous time helping them.

It is known that treatment based on feedback training may benefit patients after stroke. By providing a special information about the accuracy of studied movement, these patients may gain better control over their motor system.

It is the basic objective of the present invention to provide an apparatus for use in exercising the proper base support during gait therapy of patients with neurological disorders.

The present invention provides a device to be worn on the user's body. The device supplies audio, tactile, visual or other signals if the movement performance differs from the recommended by a physician or a physical therapist. In particular, in improvement of gait, the distance between two feet may be used as a parameter to control the base of support during therapy. Getting such an information helps to attract the user's attention and requires the user to increase the distance between feet to avoid audio, visual, or tactile signal.

A number of body and limb positions sensing devices have been developed. For example, U.S. Pat. No. 4,557,275 issued to T. Levi discloses a biofeedback system with mercury switches which produces audible or visual signals to inform the user about the changes in the position of the body. However, this system response only to change in position of the body with respect to a given plane outside of the body of the patient and therefore could not be used for assessment of step width. U.S. Pat. No. 5,433,201 issued to Mantehey discloses device for stimulating of posture and comprises a transmitter and a receiver applied to a first and second skin positions of the suitable skin area which change their mutual distances during movements of the defined body part due to the dilatation or contraction of the skin between the transmitter and the receiver. However, this device cannot be used for assessment of step width deficit because requires the dilatation or contraction of the skin between the transmitter and the receiver. Brunelle, U.S. Pat. No. 4,938,476 discloses a device worn on a part of the human body, which alerts the wearer when that body part deviates from vertical. However, the device cannot be used for assessment of step width deficit. Myers, U.S. Pat. No. 4,191,949 discloses a position warning device, associated with an otherwise conventional belt. However, the device designed for abdominal muscle control and posture optimization cannot be used for assessment of step width.

For background purposes and as an indicator of the state of the art to which the invention relates references may be made to the following remaining patents found in the search: U.S. Pat. No. 5,375,610, U.S. Pat. No. 3,208,062, U.S. Pat. No. 3,614,763.

The devices described above allow user to get information regarding the performance of certain movements. These, however, never provide information regarding step width or the position of an assistive device relative to the body of the user.

No known device for use in therapy of neurological disorders provides the ease of use and capability for stimulating (encouraging) an improvement of performance.

The object of the invention is a device and method for assessing, monitoring and feedback rehabilitation treatment programs directed towards improvement mobility of neurologically impaired people.

OBJECTIVES

As can be seen from the above discussion there is a need for a simple apparatus that allows the user to easily improve the ability to maintain normal base of support.

It is also an objective of this invention to attract the user's attention to the exercising of leg muscles, by reproducing an exercise command or musical note, serving to indicate to the user improper step width and base of support, therefore resulting in more efficient physical therapy.

It is also an objective of this invention to allow for adjustment to suit the body of a particular user, and to provide increased level of step width.

Still another objective of the present invention is to provide a method for assessment and feedback training of step width coordination that is easy to use, and an apparatus that has adjustable elements, is durable and which is relatively inexpensive to produce.

It is also considered that this invention may be used to indicate the proper position of an assistive device such as a cane, a walker, a crutch, etc., relatively to the user's body.

It is also an objective of this invention to provide patients with a method and device for self performed assessment of leg coordination during walking.

There is a need to develop a device and method to help neurologically impaired people to overcome decreased base of support and to assess biofeedback training critical to balance and locomotion skills.

BRIEF DESCRIPTION OF THE DRAWINGS

Related objectives and advantages of the present invention will become even more apparent by reference to the following figures, and to detailed description in which similar reference characters refer to similar parts.

DESCRIPTION OF THE PREFERRED EMBODIMENT

Figure 1:
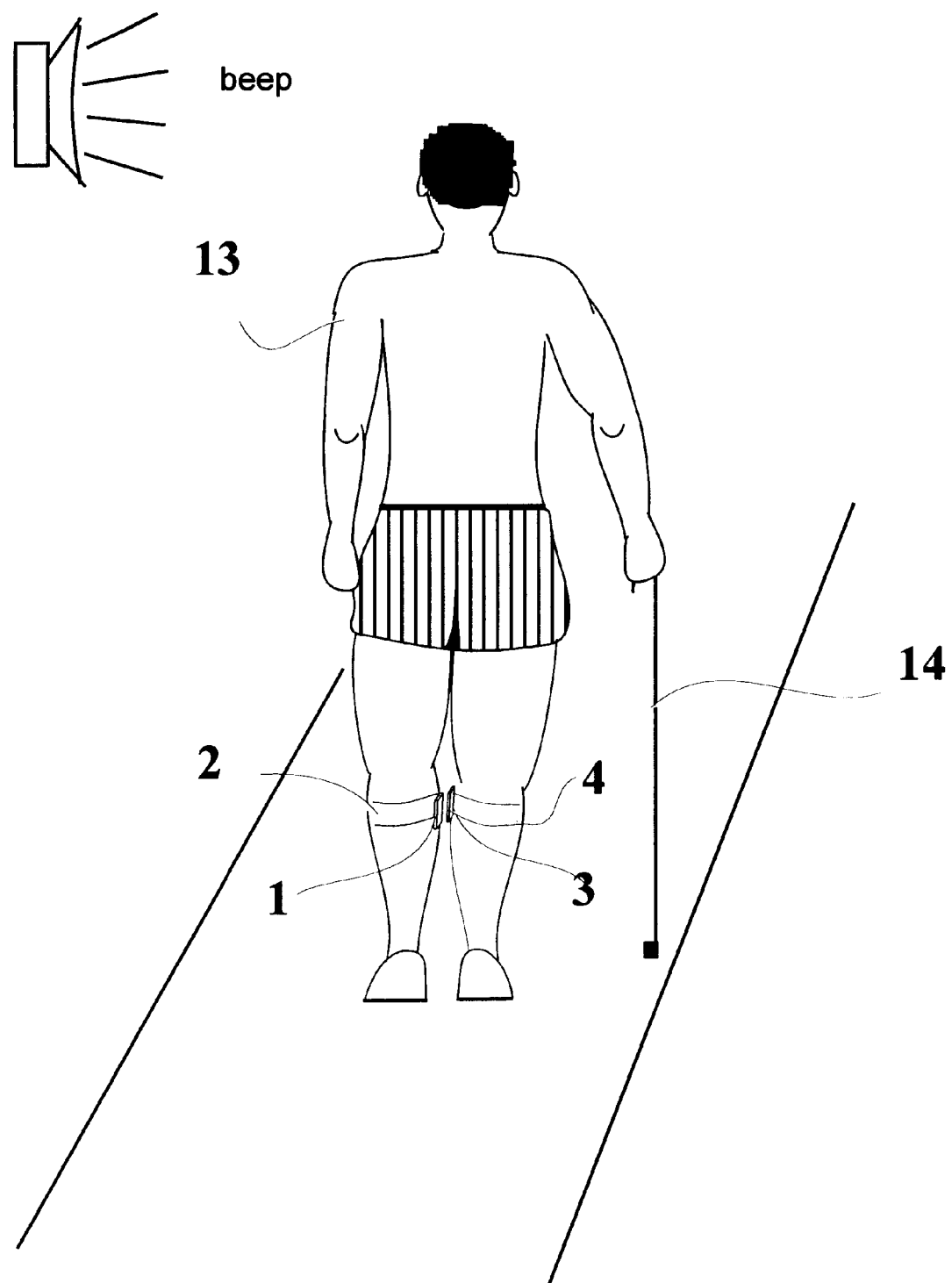
FIG. 1 is a perspective view of a device according to this invention, which is attached to the user's body and used to signalize while standing or walking with non-appropriate step width.
Figure 2:
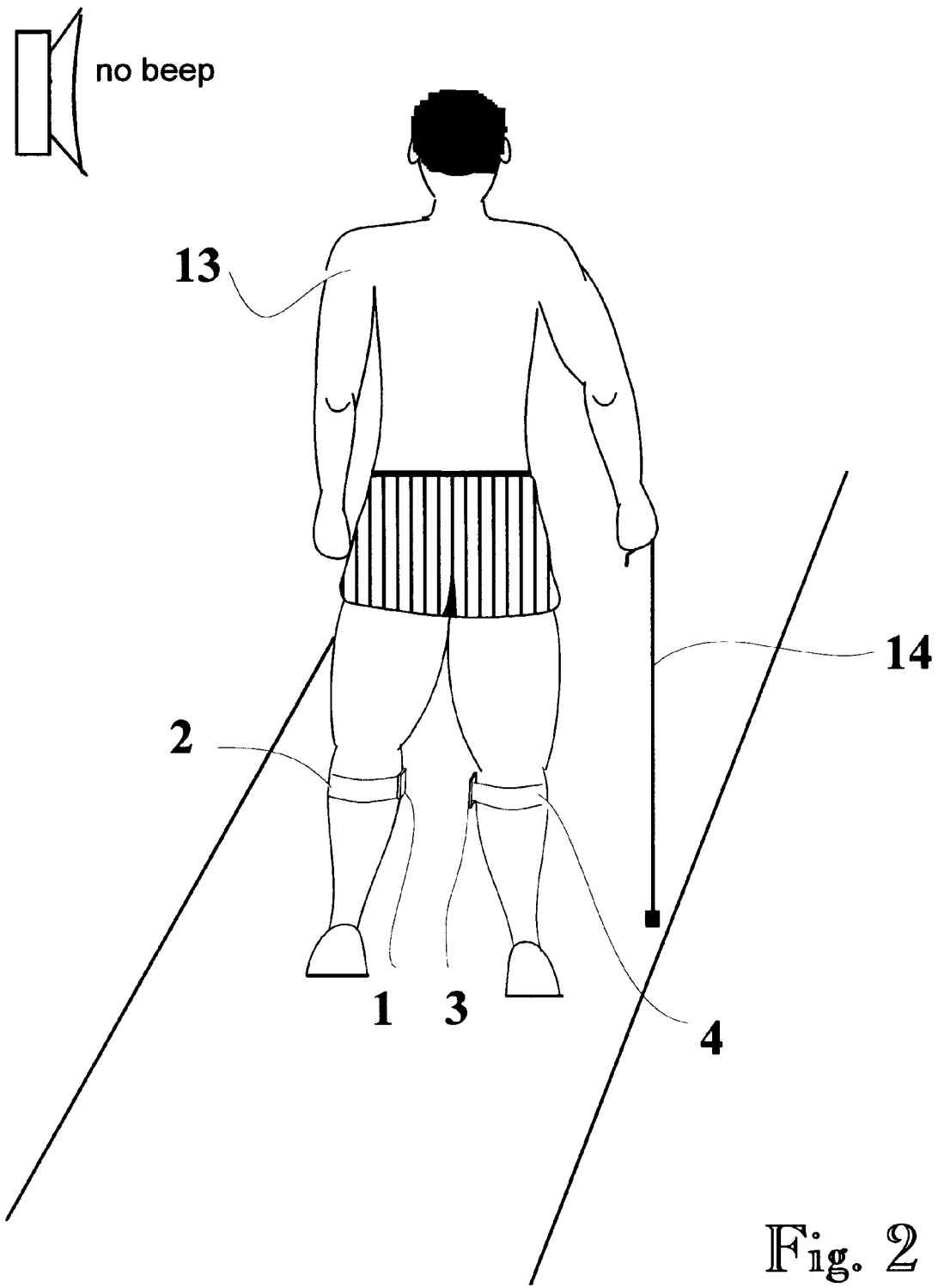
FIG. 2 is a perspective view of the device, which does not produce any signals while standing or walking with appropriate step width.
Figure 3:
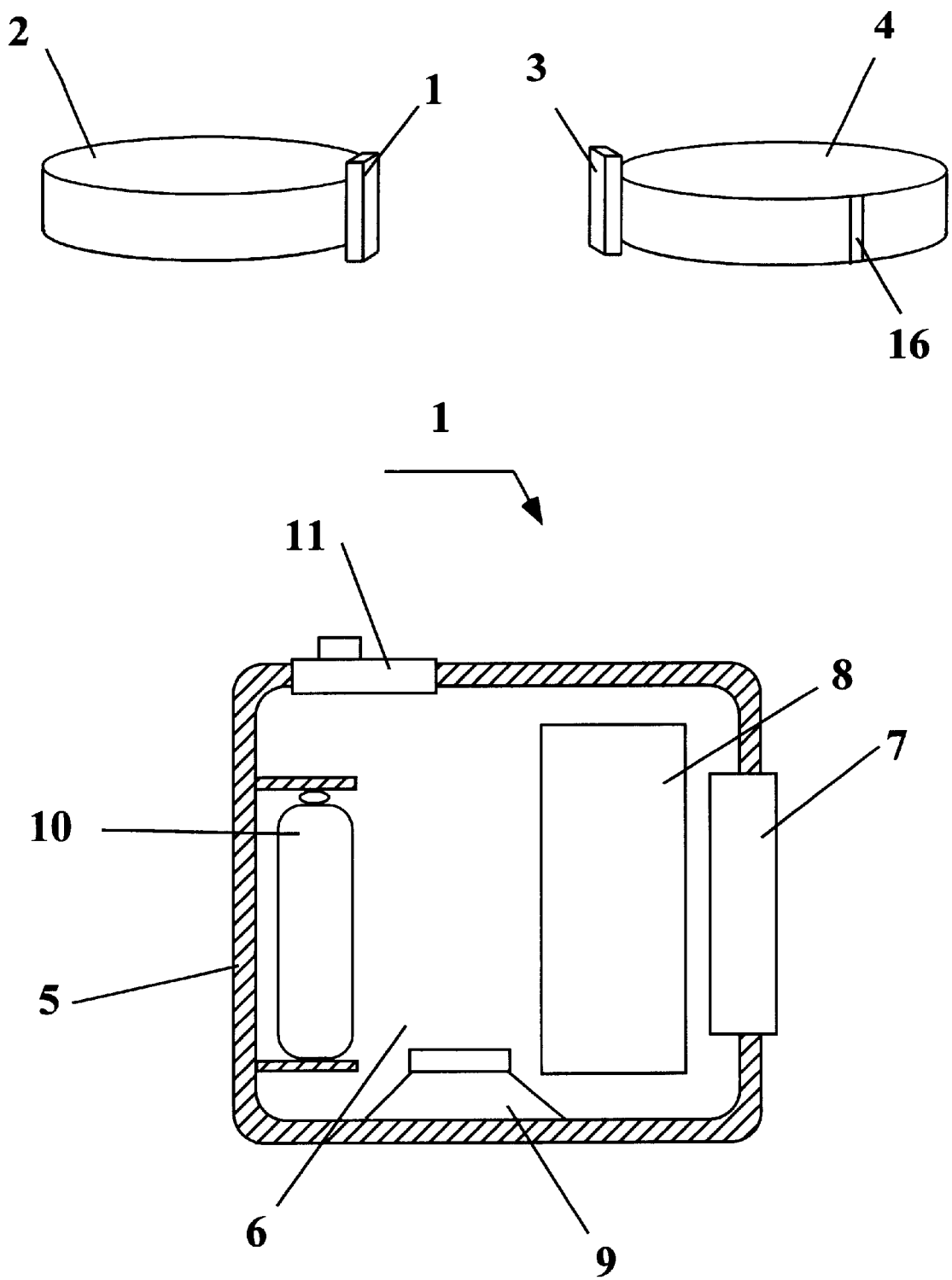
FIG. 3 is an exploded view of the receiver subsystem.

FIG. 1 shows the apparatus for assessment and biofeedback training of leg coordination according to the preferred embodiment of the invention, while the explored view of the receiving subsystem 1 is illustrated in FIG. 3. The apparatus comprises a receiver subsystem 1 connected by adjustable anchoring means 2 to one of the user's leg and a transmitter subsystem 3 connected by adjustable anchoring means 4 to the other leg of the user or to an assistive device.

The receiver subsystem 1 is composed of a box 5 having a space 6 intended to house a sensor 7, a signal-controlling circuit board 8, an announciator 9, a battery 10, and a switch 11. A cap 12 (not shown) protects the receiving space 6. The receiver subsystem 1 is designed as a flat element with oval edges helping to avoid inconvenience of use.

The anchoring means 2, 4 are designed to enable correct positioning, and retaining and adjusting the receiver subsystem 1 or transmitting subsystem 3 on the legs of the user 13 or an assistive device 14. For example, an adjustment for a proper positioning and retaining the receiver subsystem 1 or transmitting subsystem 3 may be done by adhesive or VELCRO (Registered TM) hook and loop type material positioned on the anchoring means 2, 4 (not shown). Also, the anchoring means 2, 4 may be made of any suitable or desired material. The boxes 5 and 15 (not shown) are provided and formed of any suitable flexible and resilient material and can be adjusted to fit the dimensions of a leg of the user 13.

As an illustrative example, the anchoring means 2, 4 may preferably be designed as an elastic or nonelastic belt approximately 2 inch wide and may be of any desired adjustable length which will fit both men and women (from 18" to 25"). Also, the anchoring means may be of any suitable or desired construction and material and may have any suitable closure, or buckle 16 to allow easy installation of the transmitter subsystem 1 or receiver subsystem 3 about a leg of the user 13 or an assistive device 14. This provides also unlimited adjustment of both the transmitter subsystem 1 or receiver subsystem 3 about the user's leg when standing, walking, running etc., and when different therapy or exercise protocol is applied, or when different assistive devices (cane, crutches, or walkers, etc.) are used.

Figure 4:
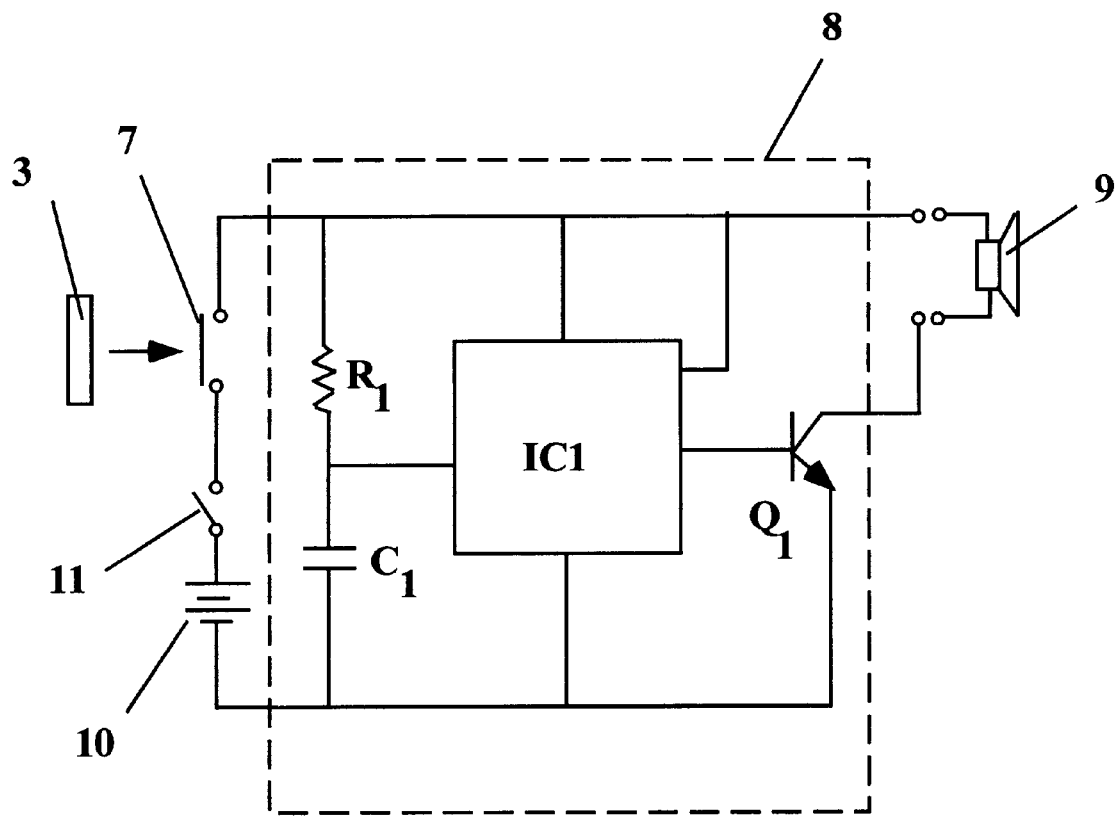
FIG. 4 is a schematic of the informing unit of the receiver subsystem.

When the receiver subsystem 1 is designed to reproduce audio information, the circuitry of the signal-controlling circuit board 8, as shown in FIG. 4, is provided with an integrated circuit (IC1) capable of storing programmable exercise commands or musical notes. The stored commands or musical sounds are reproduced through the speaker 9 in cooperation with a resistor ($R_1$), a capacitor ($C_1$), and a transistor ($Q_1$), when switch 11 is turned on and the signal from the sensor 7 is received. As an illustrative example, a magnetic switch may be used as the sensor 7. In this case the stored command or visual/tactile signal from signal-controlling circuit board 8 will appear while the switch 11 is permanently turned on and when the sensor 7 is turned on. This will happen while the emitter 14 of the transmitter subsystem 3 is brought close to the sensor 7 and activates it. Thus the distance between legs of a user will be controlled.

While the above description contains many specifics, the reader should not construe these as limitations on the scope of the invention, but merely as exemplifications of preferred embodiments thereof. Those skilled in the art will envisage many other possible variations that are within the invention scope. For example, the transmitter or receiver subsystems 1 or 3 may be installed about the leg of the user 12 with a tape 17 (not shown), the positioning and orientation of both the transmitter and receiver subsystems 1 or 3 may be different depending on the planned treatment and objectives. In particular, the transmitter and/or receiver subsystems 1 or 3 may be installed about the user's shoe or ankle, knee joints, a walker, etc.

Also, the receiving subsystem 1 may preferably be supplied with any types of announciators such as a buzzer, a regular earphone positioned on the use's ear, headphones, etc. The use of a small electrical bulb or a light-emitted diode positioned on the user's glasses frame and controlled by radio will make it easy to use by those who have a hearing problem. For the purpose of facilitating the use of the apparatus and providing reliable information to encourage the user to increase the base support, receiver subsystem 1 may be supplied with a small vibrator providing tactile information to the segment of the user's body to which the receiver subsystem 1 or transmitting subsystem 3 is attached. The vibrator also may be attached to any other part of the user's body. The vibrator also could be used as a massager having several massage protrusions on one side to produce massage applications in response to change in mutual position of the segments of the user's body with attached transmitting and sensing means. It is further understood that different position of the massager on the user's body may be used.

Figure 5:
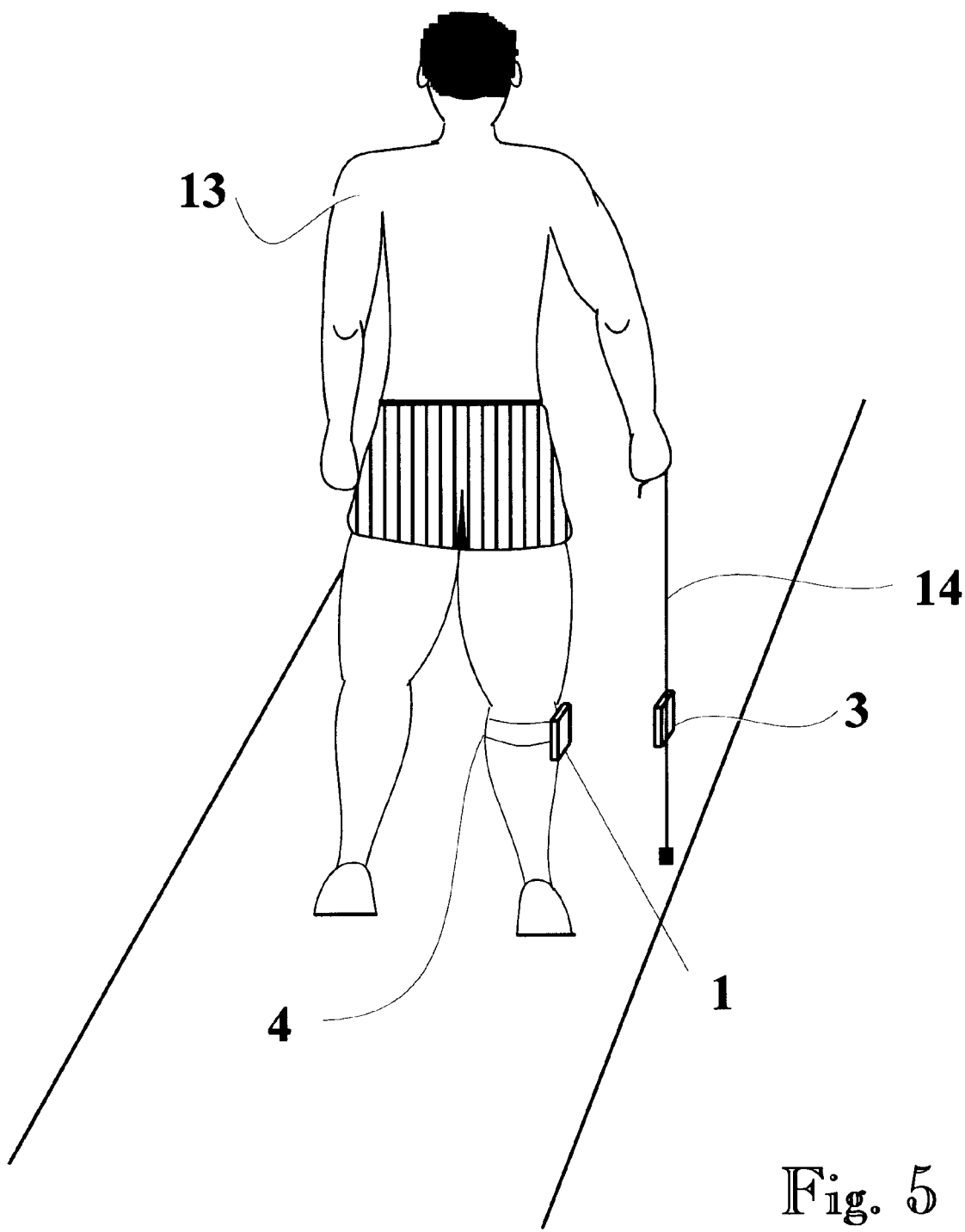
FIG. 5 is a perspective view of the device, which is used in conjunction with a cane to signalize the non-proper position of the cane with respect to the body of the user.

Another example of using the device for assessment and feedback training is described below and illustrated by FIG. 5. The transmitting subsystem 3 could be positioned on the leg of the user 13 as it was previously described, while the receiving subsystem 1 is positioned on an assistive device, for example on a cane 14. While the user 13 uses inappropriate position of the cane 14, for example the cane 14 is too close to the user's body, the device will provide a signal. This will encourage the user to improve the position of the cane 14 relatively to the user's body. Similar effect will be achieved while one part of the device is positioned on a crutch, walker, a stick, etc.

Another example of the development of the device is providing it with a sensor sensitive to a movement of anything, which is "visible" to the sensor. In this case the device will include only the receiving subsystem 1 positioned on one leg of the user 13. The moving sensor will recognize the other leg of the user or the assistive device while they are brought closer then previously established threshold. This produces a signal encouraging the user to adjust the position of legs or the assistive device.

The device uses limited by the distance the control signal can travel: the system functions only within a specific operational radius. This radius extends from 1 to 25 inches, depending on the dimensions of a particular user and treatment protocol. When the distance between the receiver subsystem 1 and the transmitter subsystem 3 is more than control radius, the device is in stationary condition and the control circuit does not produce a signal. When the distance between two subsystems 1, 3 became less then the operational radius, the signal from the transmitter 3 activates the receiver 1 producing a signal, which activates the circuit reproducing an exercise command.

The spectrum of technologies which can be used in designing the device includes the entire range of wavelengths of frequencies of electromagnetic radiation extending from gamma rays and radio waves to the visual light spectrum. It is further understood that different schemes including infrared, radio, ultrasound, etc. may be used to build the device, and the particular scheme will influence the particular design and applicability with patients without limiting the idea of the invention. The base receiver can be configured to accept signals from variety of signal sources such as infrared, radio frequency, magnetic field, visual light, etc.

It is further understood that any corresponding mechanical, electrical, mechano-electrical, optical, magneto-electrical and other sensors could be used for designing the device as well as the particular location of the elements of the device along the user's body or along the assistive devise is possible.

The apparatus also may be supplied with an electrical stimulator, which delivers single, repetitive, twin, etc. pulses to hip abductor or other muscles providing appropriate training of these muscles. In this case, the sensor 7 provides activation of the electrical stimulator when the distance between two legs is less than it was previously established by a physical therapist of by the user.

OPERATION OF THE INVENTION

To use the apparatus, a user should first install the receiver subsystem 1 about the leg using anchoring elements 2. Then the transmitter subsystem 3 should be installed about the other leg of the user 13 with anchoring elements 4. The anchoring elements 2, 4 and buckles 16 will provide positioning of both the receiving and transmitting subsystems 1, 3 on the user's body. As an example we describe the operation of the invention when the magnetic switch is used as the sensor 7. A position of the legs of the user 13 close to each other will bring a magnetic field of the emitter of the transmitter 3 to the magnetic switch 7 of the receiver 1. This will turn the switch 7 on, activating the signal-circuit unit 8 and producing a sound, visual, tactile or other signal depending on the particular structure of the apparatus. In response, the user should bring the legs farther, which will release activation of the switch 7 and stop the production of any audio/visual, tactile, or other signals. This will inform the user about the desired goal. By changing, for example, the sensitivity of the receiver 1, the user will adjust the apparatus to his/her particular exercise protocol. A receiving subsystem 1 could be also installed about an assisstive device 14 while the transmitting subsystem 3 is installed about the body of the user or vice versa. The signal from the transmitting subsystem 3 will reach receiving unit 1 when the user 13 brings legs or an assistive device 14 close enough. These will produce a signal encouraging the user to increase the base of support or improve the position of the assistive device with respect to the body. These will lead avoiding the sound, visual/tactile, or other signal.

If the signal from the receiving subsystem 1 is present all the time, even when the position of legs is far enough, or the location of the assistive device, for example a cane, is proper, the threshold of the receiving subsystem 1 should be decreased. When there is no signal from receiving subsystem 1 while legs are close to each other or the assistive device 14 is close enough, the threshold of the system should be increased. Since the threshold is adjusted, the user may perform walking exercises for appropriate time.

The position of the device on the user's body may be different depending on the desired protocol of rehabilitation or physical therapy. For example, if the user wants to improve the position of an assistive device such as a cane, walkers, etc., the device will be positioned in respect with this assistive device. If the user is interested in increasing a step width, the device will be positioned on one or both legs of the user 13 depending on the particular sensor system is used. As an example, the receiving subsystem 1 could be positioned on the upper shin of one leg just below the knee, while the transmitting subsystem 3 could be positioned on the upper shin of the other leg just below the knee. Changing the location of sensing or transmitting subsystems from anterior to more lateral/medial positions will alter the sensitivity of the device. If the user is interested in improving of arm movements during locomotion and, in particularly, the position of the hand respectively to the position of the body, the receiver subsystem 1 may be positioned on the body of the user 13, for example on the thigh, and the transmitter subsystem 3 could be positioned on the palm of the hand. Accordingly, the scope of the invention should be determined not by embodiment illustrated, but by the appended claims and their legal equivalents.

What I claim is:

1. An apparatus for assessment and feedback training of step width coordination comprising: a first anchoring means, at least one sensing means which is adapted to be removably fixed to a first body part of a user with said first anchoring means, a second anchoring means and a transmitting means adapted to be removably fixed to a second body part with said second anchoring means, the first anchoring means including a band adapted to be secured around the first body part and to retain the sensing means to said first body part and the second anchoring means including a band adapted to be secured around the second body part and to retain the transmitting means to said second body part, the sensing means and the transmitting means being in an orientation substantially opposing each other, the transmitting means being oriented to provide a radiated signal when said transmitting means is fixed to said second body part by said second anchoring means, said sensing means being adapted to receive said radiated signal, and said sensing means is supplied with signal processing means, said signal processing means producing at least one of a visual, audible and tactile signal in response to change in mutual position between first and second body parts of the user's body with attached transmitting and sensing means, and at least one of said transmitting and said sensing means having elements to adjust sensitivity of the apparatus.

2. An apparatus for assessment and feedback training of step width coordination comprising: a first anchoring means, at least one sensing means which is adapted to be removably fixed to a user's body with said first anchoring means, a second anchoring means, and a transmitting means adapted to be removably fixed to an assistive device with said second anchoring means; said sensing means is supplied with signal processing means, said signal processing means producing at least one of a visual, audible and tactile signal in response to change in mutual position of the assistive device with attached transmitting means with respect to the element of the user's body with attached sensing means, and at least one of said transmitting and said sensing means having elements to adjust sensitivity of the apparatus.

3. An apparatus for assessment and feedback training of step width coordination of claim 1, wherein said sensing means comprise a combination of active and/or passive sensitive elements.

4. An apparatus for assessment and feedback training of step width coordination of claim 1, wherein said sensing means is distance sensitive, and said signal processing means is operable for developing distinctive signals resulting from changes in inter segmental distance.

5. An apparatus for assessment and feedback training of step width coordination of claim 1 or claim 2, wherein said signal processing means produces at least one of acoustic, visual, tactile, and electrical effects.

6. An apparatus for assessment and feedback training of step width coordination of claim 2, wherein said transmitting means is adapted to be removably fixed to the user's body with said first anchoring means and the sensing means is adapted to be removably fixed to an assistive device.

7. A method for assessment and feedback training of step width coordination comprising the steps of:
   providing a device comprised of:
      a sensing means having a sensor, an announciator with a signal-controlling circuit and a signal reproducer, a switch, an electrical power source, and anchoring elements to retain said sensing means on the user's body; and
      transmitting means having an emitter, a switch, an electrical power source, and anchoring elements to retain said transmitting means on the body of the user;
   placing the transmitting means on one segment of the user's body and securing with anchoring means;
   placing the sensing means on another segment of the user's body and securing with anchoring means;
   turning on switches of said transmitting and sensing means;
   activating the sensor of said sensing means by bringing the parts of the user's body with said transmitting and sensing means close enough until said signal reproducer reproduces a signal;
   adjusting the threshold of the either one or both the transmitting or sensing means relatively to a particular exercise protocol or desired distance between two elements of the user's body with said transmitting and sensing means;
   drawing the body elements with said transmitting and sensing means away from each other to deactivate the sensor and thereby terminate the signal from the announciator;
   conversely, performing desired physical activity based on not getting a signal from said signal reproducing means which means that a required distance between two body parts is in required limits;
   turning off the switches when the session is finished.

8. A method for assessment and feedback training of step width coordination comprising the steps of:
   providing a device comprised of:
      a sensing means having a sensor, an announciator with a signal-controlling circuit board and a signal reproducer, a switch, an electrical power source, and anchoring elements to retain said sensing means on the user's body;
      a transmitting means having an emitter, a switch, an electric power source, and anchoring elements to retain said emitting means on an assistive device;
   placing the sensing means on one segment of the user's body and securing with anchoring means;
   placing the transmitting means on the assistive device and securing with anchoring means;
   turning on switches of said transmitting and sensing means;
   activating the sensor of said sensing means by making the assistive device with said transmitting means close enough until said signal reproducer reproduces a signal;
   adjusting the threshold of the either one or both the transmitting or sensing means relatively to a particular exercise protocol or desired distance between the user's body and the assistive device;
   drawing the assistive device with said transmitting means away from the body to deactivate the sensor and thereby terminate the signal from the announciator;
   conversely, performing desired physical activity based on not getting a sign al from said signal reproducing means which means that a required distance between the body and the assistive device is in required limits;
   turning off the switches when the session is finished.

9. A method for assessment and feedback training of step width coordination of claim 8 wherein said sensing means is placed on the assistive device and the transmitting means is placed on the user's body.

10. An apparatus for assessing step width coordination comprising:
   a first anchoring member having at least one sensor, the first anchoring member including a band adapted to be removably secured around a first body part for securing said sensor to said first body part;
   a second anchoring member having a transmitter, the second anchoring member including a band adapted to be removably secured around a second body part and to retain said transmitter in an orientation with respect to said second body part to provide a radiated signal away from a surface of said second body part and toward said sensor; and
   wherein the sensor is adapted to receive said radiated signal and to produce a signal in response to a change in position between the first and second body parts.

11. The apparatus of claim 10, wherein the sensor comprises a signal processor.

12. The apparatus of claim 11, wherein the signal processor produces signals in response to the distance changes between the first and second body parts.

13. The apparatus of claim 11, wherein the signal processor produces at least one of visual, electric or tactile effects.

14. The apparatus of claim 10, wherein at least one of the transmitter and the sensor comprises elements for adjusting sensitivity of the apparatus.

15. The apparatus of claim 14, wherein the elements comprise at least one of a passive element and an active element.

16. The apparatus of claim 10, wherein the sensor is distance sensitive.

17. The apparatus of claim 10, wherein the transmitter is adapted to be removably fixed to the first body part and the sensor is adapted to be removably fixed to the second body part.

18. An apparatus for assessing step width coordination comprising:
   a first anchoring member having at least one sensor, the first anchoring member adapted to be removably fixed to a first body part;
   a second anchoring member having a transmitter, the second anchoring member adapted to be removably fixed to a device; and
   wherein the sensor produces a plurality of signals in response to a change in position between the first body part and the device.

19. The apparatus of claim 18, wherein the device is independently movable from the first body part.

20. The apparatus of claim 18, wherein the sensor comprises a signal processor.

21. The apparatus of claim 20, wherein the signal processor produces signals in response to distance changes between the first body part and the device.

22. The apparatus of claim 20, wherein the signal processor produces at least one of visual, electric or tactile effects.

23. The apparatus of claim 18, wherein at least one of the transmitter and the sensor comprises elements for adjusting the sensitivity of the apparatus.

24. The apparatus of claim 18, wherein the sensor is distance sensitive.

25. The apparatus of claim 18, wherein the transmitter is adapted to be removably fixed to the first body part and the sensor is adapted to be removably fixed to the device.

26. A method for assessing step width coordination comprising the steps of:
   securing a sensor to a first body part with a first anchoring member;
   securing a transmitter to a second body part independently movable from the first body part with a second anchoring member;
   turning on a switch of the transmitter and a switch of the sensor;
   activating the sensor by moving the transmitter in a first direction and the sensor in a second direction opposite the first, thereby producing a signal;
   adjusting the sensor to a desired sensitivity level;
   performing physical activity within boundaries of the sensitivity level;
   deactivating the sensor by moving the transmitter in the second direction and the sensor in the first direction opposite the second; and
   turning off the transmitter and sensor switches.

27. The method for assessing step width coordination of claim 26, wherein the sensor is secured to the second body part and the transmitter is secured to the first body part.

28. The method of claim 26, wherein the sensor is adjusted to a desired sensitivity level, based on the distance between the transmitter and sensor.

29. The method of claim 26, wherein the transmitter is adjusted to a desired sensitivity level, based on the distance between the transmitter and sensor.

30. A method for assessing step width coordination comprising the steps of:
   securing the sensor to a first body part with a first anchoring member;
   securing the transmitter to a device with a second anchoring member;
   turning on the sensor switch and the transmitter switch;
   activating the sensor by moving the transmitter in a first direction and the sensor in a second direction opposite the first direction, thereby producing a signal;
   adjusting the sensor to a desired sensitivity level, based on the distance between the transmitter and sensor;
   performing physical activity within boundaries of the sensitivity level;
   deactivating the sensor by moving the transmitter in the second direction and the sensor in the first direction opposite the second; and
   turning off the transmitter and sensor switches.

31. The method for assessing step width coordination of claim 30, wherein the sensor is secured to the device and the transmitter is secured to the first body part with the first anchoring member.

32. The method of claim 30, wherein the sensor is adjusted to a desired sensitivity level, based on the distance between the transmitter and sensor.

33. The method of claim 30, wherein the transmitter is adjusted to a desired sensitivity level, based on the distance between the transmitter and sensor.

* * * * *

UNITED STATES PATENT AND TRADEMARK OFFICE
CERTIFICATE OF CORRECTION

PATENT NO. : 6,234,982 B1
DATED : May 22, 2001
INVENTOR(S) : Alexander S. Aruin

It is certified that error appears in the above-identified patent and that said Letters Patent is hereby corrected as shown below:

Column 8,
Line 27, after "not getting a" delete "sign al" and insert -- signal --.

Signed and Sealed this

Eighth Day of January, 2002

Attest:

Attesting Officer

JAMES E. ROGAN
Director of the United States Patent and Trademark Office